US008142391B2

(12) United States Patent
Mitchell

(10) Patent No.: US 8,142,391 B2
(45) Date of Patent: Mar. 27, 2012

(54) ELECTROSTATIC TRANSCUTANEOUS HYPODERMIC SPRAY (ELECTROSTATIC HYPOSPRAY)

(76) Inventor: Stuart B. Mitchell, Lake Forest Park, WA (US)

( * ) Notice: Subject to any disclaimer, the term of this patent is extended or adjusted under 35 U.S.C. 154(b) by 0 days.

(21) Appl. No.: 11/992,149

(22) PCT Filed: Nov. 21, 2006

(86) PCT No.: PCT/US2006/061159

§ 371 (c)(1), (2), (4) Date: Mar. 17, 2008

(87) PCT Pub. No.: WO2007/073527

PCT Pub. Date: Jun. 28, 2007

(65) Prior Publication Data

US 2009/0054831 A1 Feb. 26, 2009

Related U.S. Application Data

(60) Provisional application No. 60/740,425, filed on Nov. 29, 2005.

(51) Int. Cl.
*A61M 31/00* (2006.01)

(52) U.S. Cl. ................ 604/68; 604/69; 604/70; 604/71; 604/20; 604/24; 239/708

(58) Field of Classification Search ............. 604/68–72, 604/20, 24; 239/708
See application file for complete search history.

(56) References Cited

U.S. PATENT DOCUMENTS

| | | | | |
|---|---|---|---|---|
| 2,479,888 | A * | 8/1949 | Wyld et al. | 60/39.281 |
| 3,527,216 | A * | 9/1970 | Snyder | 604/88 |
| 3,873,024 | A * | 3/1975 | Probst et al. | 239/704 |
| 4,121,593 | A * | 10/1978 | Kastrubin et al. | 607/46 |
| 4,680,027 | A | 7/1987 | Parsons et al. | |
| 4,821,509 | A * | 4/1989 | Burton et al. | 60/203.1 |
| 4,945,050 | A | 7/1990 | Sanford et al. | |
| 5,024,656 | A | 6/1991 | Gasaway et al. | |
| 5,247,842 | A | 9/1993 | Kaufman et al. | |
| 5,630,796 | A | 5/1997 | Bellhouse et al. | |
| 6,093,557 | A * | 7/2000 | Pui et al. | 435/173.1 |
| 6,478,771 | B1 * | 11/2002 | Lavi et al. | 604/82 |
| 6,641,553 | B1 | 11/2003 | Chee et al. | |
| 7,207,967 | B1 * | 4/2007 | Bellhouse et al. | 604/70 |
| 2001/0001452 | A1 * | 5/2001 | Moon et al. | 210/198.2 |
| 2004/0215135 | A1 | 10/2004 | Sheldrake et al. | |
| 2005/0154369 | A1 | 7/2005 | Broullette et al. | |
| 2006/0041248 | A1 | 2/2006 | Patton et al. | |

* cited by examiner

*Primary Examiner* — Bhisma Mehta
*Assistant Examiner* — Edelmira Bosques
(74) *Attorney, Agent, or Firm* — Randall W. Chang

(57) ABSTRACT

A method and apparatus for delivering therapeutic or diagnostic agents as a low pressure high velocity spray into tissue. According to the particular desired spray characteristics, the spray may be generated via the combined use of pressure atomization and electrostatic spray charging, or via the combined use of pressure atomization and electrostatic atomization. Particle velocity, spray flow-rate, and spray dispersion are further controlled via electrostatic means.

30 Claims, 13 Drawing Sheets

Dose Metering Stage

Dose Injecting Stage

Dose Metering Stage

Dose Injecting Stage

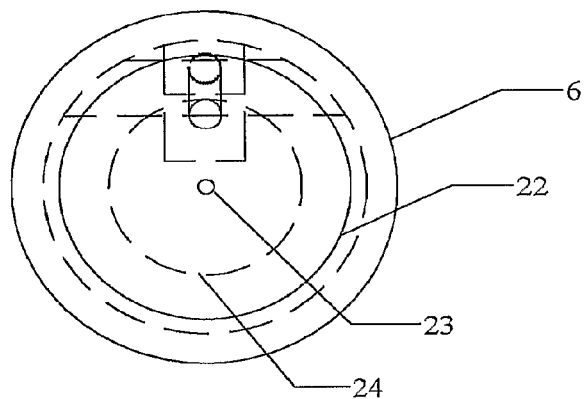
FIG. 12A
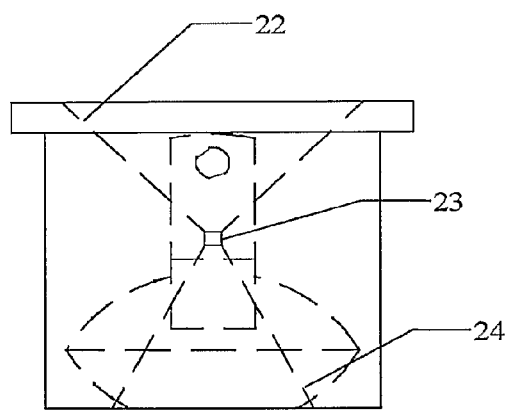 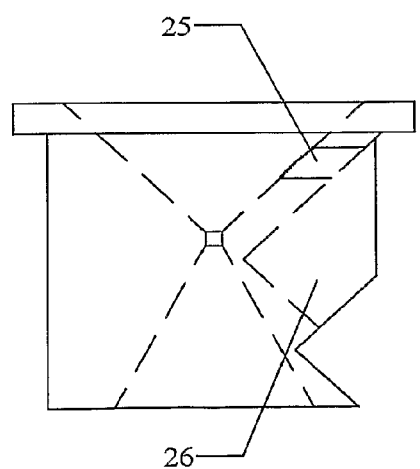
FIG. 12B  FIG. 12C

ELECTROSTATIC TRANSCUTANEOUS HYPODERMIC SPRAY (ELECTROSTATIC HYPOSPRAY)

CROSS-REFERENCE TO RELATED APPLICATIONS

This application claims the benefit of priority of U.S. Provisional Application Ser. No. 60/740,425, filed Nov. 29, 2005, entitled "Electrostatic Transcutaneous Hypodermic Spray (Electrostatic Hypospray)" which is incorporated herein by this reference.

TECHNICAL FIELD

The present invention relates generally to an apparatus and method for injecting an agent into tissue. More particularly the present invention relates to an apparatus and method utilizing pressure atomization combined with electrostatic acceleration of the spray particles for accomplishing such.

BACKGROUND ART

Two problems affecting world health (particularly in third world countries) are diabetes and vaccinations for disease prevention. Vaccination programs depend on the availability of syringes or hypodermics. Some diabetics face the traumatic and painful prospect of daily insulin injections. There is a need for a less painful injection alternative.

One type of needleless hypodermics are jet injectors. Such jet injectors on the market use either compressed gas or compression springs to generate a high velocity jet (diameters ranging between 76 to 360 μm) to penetrate the skin. These devices obtain fluid velocities between 80 to 190 m/s and generate up to 600 W of power. Typical delivery volumes range between 0.05 and 1 cc. To use these devices the users have to transfer the drugs from their original vials to the devices. In addition, the jet injectors typically deliver the dose in the form of a stream rather than spray. With jet injectors, a fluid pocket forms under the dermis. Backflow may result if the pressure in the pocket exceeds the flow pressure, potentially causing cross-contamination. In addition, doses delivered as a spray would be absorbed more readily than a pocket of fluid. However, jet injectors do not deliver a consistent dose; they involve multi-step processes to use; they induce pain (due to the high pressure); and are susceptible to cross-contamination during transfer. Thus, the devices on the market are typically designed as single-use devices usually used by individuals to avoid anaphylactic or insulin shock. That is, individuals pre-load the devices and carry them around in case of an emergency situation.

In order to avoid the shortcomings of jet injectors, some developers of needleless hypodermics have looked to electrospray technology. Issued U.S. Pat. No. 6,093,557 discloses a method for electrostatically creating a spray of charged particles for delivery into cells. Issued U.S. Pat. No. 4,945,050 discloses a method for electrostatically accelerating particles into cells.

SUMMARY OF INVENTION

An object of the present invention is to provide a device capable of delivering a variety of therapeutic and/or diagnostic agents at consistent repeatable doses, without pain, or the use of hypodermic needles. Another object of the present invention is to provide a device that operates at low pressure, yet delivers a spray at high velocity to ensure effective penetration into tissue. Another object of the present invention is to provide a device capable of multiple injections without the risk of cross-contamination or repeated refilling after each injection. Another object of the present invention is to provide an improved means for creating a particle spray and accelerating the particles for delivery into tissue. Another object of the present invention is to create a spray of nanometer sized particles which would require lower velocities for tissue/dermal penetration than micron sized particles.

In the present invention, a spray is generated from a fluid by pressure atomization (with inherent particle acceleration), with the fluid particles further accelerated by electrostatic acceleration due to charge imparted by electrostatic spray charging. Pressure atomization provides a mechanism for atomizing the fluid into particles and imparting a finite exit velocity to the particles. In other embodiments, atomization occurs by both pressure atomization and by electrostatic atomization (which inherently includes electrostatic spray charging), achieving superior atomization than by either mode alone. In further embodiments, one or more electrodes placed downstream of the atomization region serve to: a) accelerate the particles; b) decelerate the particles, c) focus the spray d) disperse the spray; e) combination of the foregoing.

The agent to be injected is in the form of a fluid (solution or suspension), capable of being atomized by pressure atomization. The agent may be a therapeutic agent, diagnostic agent, or combination of the foregoing. In certain embodiments, the agent may be contained ill one or more reservoirs. In other embodiments, the constituent components of the agent are contained in two or more reservoirs, wherein the components are combined to form the agent.

BRIEF DESCRIPTION OF DRAWINGS

FIGS. 12A-12C present top, front, and side views of an embodiment of the nozzle.

In the figures, like or similar elements (such as capillary 3) utilize the same reference characters throughout the various views.

BEST MODES FOR INVENTION

Figure 1A:
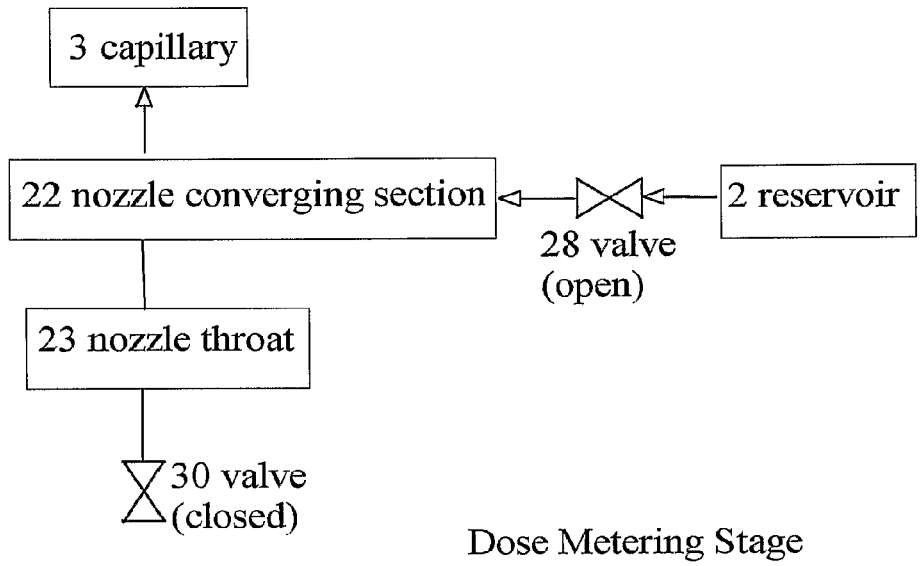
FIGS. 1A and 1B illustrate the dose metering and injecting stages of an embodiment wherein the fluid is pressurized in the nozzle and capillary.

Definitions:

| | |
|---|---|
| electrostatic atomization | atomization of a fluid due to electrostatic forces exerted by an applied electric potential |
| electrostatic spray charging | electrostatic charge imparted to particles due to an applied electric potential |
| pressure atomization | atomization of a fluid due to pressure differences as a high pressure fluid is passed through a small orifice to a region of lower pressure |

In the present invention, a spray is generated from a fluid by pressure atomization (with inherent particle acceleration), with the fluid particles further accelerated by electrostatic acceleration due to charge imparted by electrostatic spray charging. Pressure atomization provides a mechanism for atomizing the fluid into particles and imparting a finite exit velocity to the particles. Thus none of the energy from the applied electric potential need go towards atomizing the fluid, but can then fully go towards accelerating the particles further. In further embodiments, atomization occurs by both pressure atomization and by electrostatic atomization, achieving superior atomization than by either mode alone. It should be noted that electrostatic atomization inherently includes electrostatic spray charging as well. Embodiments incorporating pressure atomization and electrostatic atomization would require higher voltages than pressure atomization and electrostatic spray charging. In further embodiments, one or more electrodes placed downstream of the atomization region serve to: a) accelerate the particles; b) decelerate the particles, c) focus the spray d) disperse the spray; e) combination of the foregoing.

In embodiments of the present invention, the agent to be injected is contained in one or more reservoirs. In certain embodiments of the present invention, the reservoir comprises a standard sized vial of agent which may be inserted into the inventive device. Standard vials would typically include (but not limited to) 5, 10, 20, 50, 100cc sizes. In certain embodiments, once the vial is inserted, a septum on the vial is pierced (in further embodiments by automated means), to allow for fluid removal. In other embodiments, the reservoir comprises a non-standard sized container having a fluid communication interface with the inventive device.

In embodiments of the present invention, the agent to be injected is in the form of a fluid, (solution or suspension). The agent may be any fluid capable of being atomized by pressure atomization. In further embodiments of the present invention, the agent is intended to be injected as a spray. In still further embodiments, the agent comprises a therapeutic agent, a diagnostic agent, or combination of the foregoing.

In further embodiments, the agent to be injected comprises components contained in two or more reservoirs, wherein the components are combined to form the agent.

The components may comprise the constituent parts to an agent (e.g. a reconstituted virus vaccine), fully constituted agents (e.g. various insulin formulations), or combinations of the above. The components may include but not limited to multiple drugs, vaccines, other therapeutic agents, diagnostic agents, and combination of the foregoing. In one embodiment, the agent is a vaccine derived from live-viruses that are purified, concentrated and dried by lyophilization. The vaccine results from reconstitution of the virus with glycerin, phenol in sterile water. In another embodiment, a diabetic may select a combination of long-lasting insulin and short-acting insulin. Although premixed versions (70/30 or 50/50) vials are available, in some instances these premixed versions may not be desired. In another embodiment, lidocaine (anesthetic typically used in a two percent solution) is combined with epinephrine (a vasoconstrictor).

In still further embodiments, one or more of the components is in the dry state that are then combined with other agent components to form the agent to be injected. Such dry state components may include but not limited to: the lyophilized virus discussed above, dry components to be dissolved into solution, and dry components that form a suspension with fluid agent components. In the case of lyophilized virus, one could dispose glycerin, phenol and water in one vial, and the lyophilized virus in another vial. Examples of other dry components may include but not limited to: certain antibiotics, steroids and chemotherapy drugs that require mixing prior to use. In embodiments where the dry component is contained in one vial, and the fluid component contained in another vial, various means may be used to combine the components. In one embodiment, the fluid component is drawn into the capillary, then transferred into the vial with the dry component. The resulting solution is drawn back into the capillary from where it is then sent through the nozzle and injected. In another embodiment, the fluid component is transferred into the vial with the dry component, from which it is then drawn into the capillary and injected.

Figure 1B:
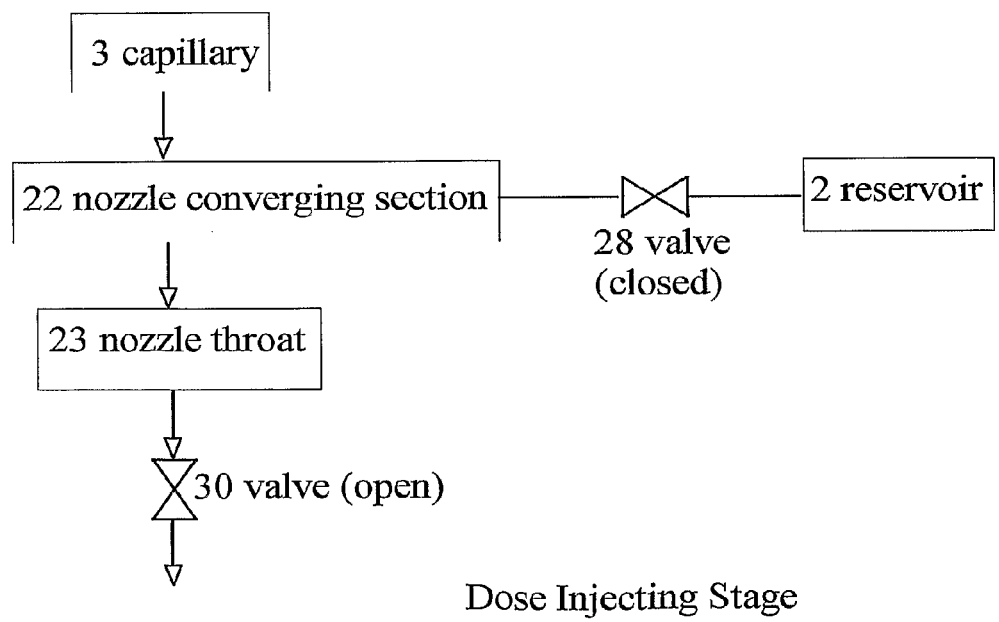

Referring to FIGS. 1A and 1B, in certain embodiments, a valve 28 ('reservoir valve') is located between the reservoir 2 and the nozzle converging region 22 which can be closed to prevent flow back into the reservoir 2. A second valve 30 ('throat valve') is located in the nozzle throat region 23 to prevent flow during the dose metering/pressurizing stage. Referring to FIG. 1A, a metered amount of agent ('dose') is drawn from the reservoir 2 into the converging section 22 of the nozzle (reservoir valve 28 open, throat valve 30 closed). Depending on the size of the dose, some of the dose may be drawn up into the capillary 3 as well. The agent dose is pressurized to a designated pressure (reservoir valve 28 closed, throat valve 30 closed). Referring to FIG. 1B, the reservoir valve 28 is closed, the throat valve 30 is opened, and the agent dose is forcibly expelled through the nozzle throat 23.

Figure 2A:
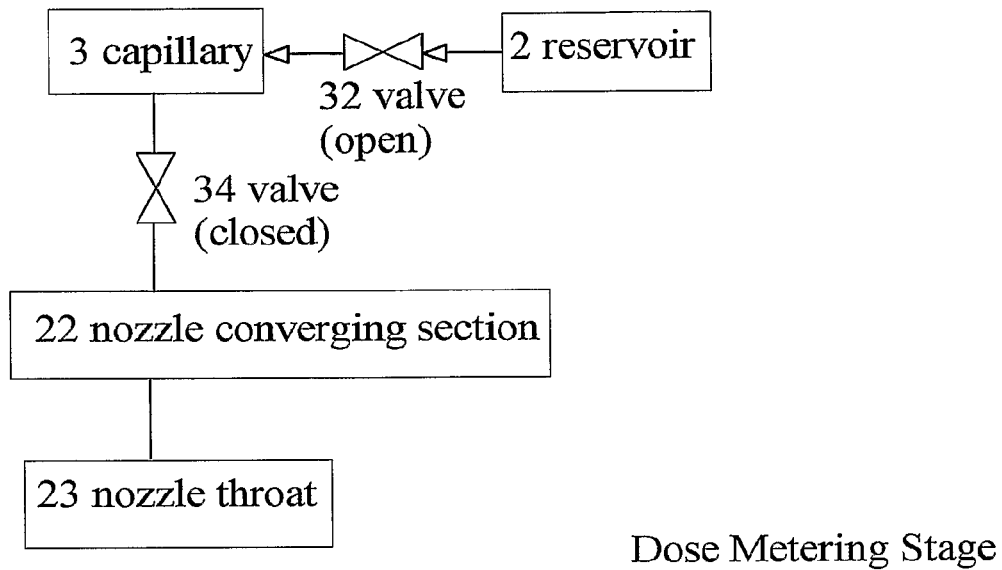
FIGS. 2A and 2B illustrate the dose metering and injecting stages of an embodiment wherein the fluid is pressurized in the capillary.
Figure 2B:
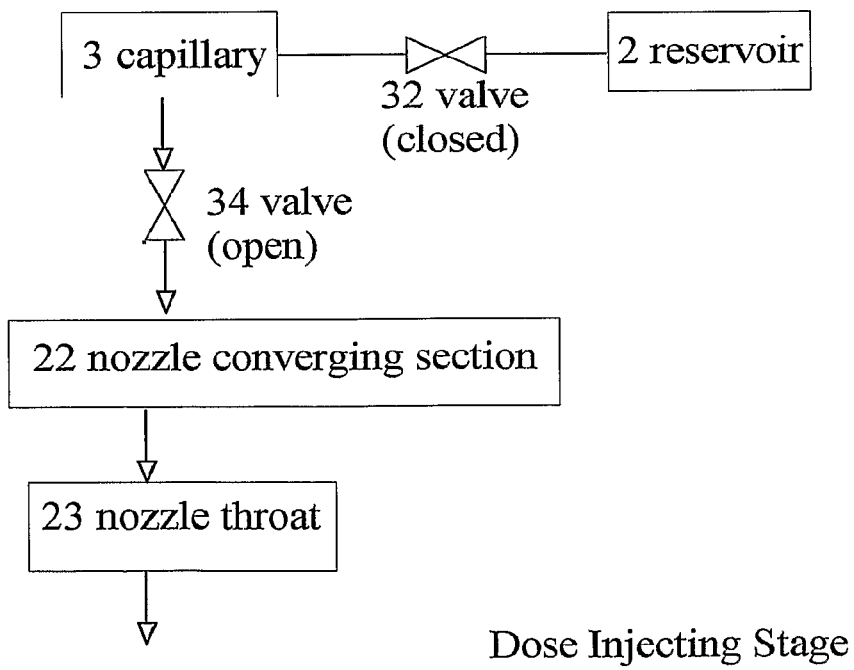

Referring to FIGS. 2A and 2B, in certain embodiments, a valve 32 ('reservoir valve') is located between the reservoir 2 and the capillary 3 which can be closed to prevent flow back into the reservoir 2. A second valve 34 ('capillary valve') is located between the capillary 3 and the nozzle converging region 22. Referring to FIG. 2A, a metered amount of agent ('dose') is drawn from the reservoir 2 into the capillary 3 (reservoir valve 32 open, capillary valve 34 closed). The agent dose is pressurized (reservoir valve 32 closed, capillary valve 34 closed). Referring to FIG. 2B, the reservoir valve 32 is closed, the capillary valve 34 is opened, and the agent dose is forcibly expelled into the nozzle converging section 22, and through the nozzle throat 23.

In certain embodiments, said reservoir valves are unidirectional valves which automatically prevent flow back into the reservoir. In other embodiments, the reservoir valves are valves which are opened or closed by active control. In various embodiments (as illustrated in FIGS. 1A, 1B, 2A and 2B), the use of two discrete valves (e.g. reservoir valve and throat valve, or reservoir valve and capillary valve) is disclosed. It is to be understood that the two valve functions may be also be accomplished with a single valve structure as would be known to those skilled in the art.

Figure 3A:
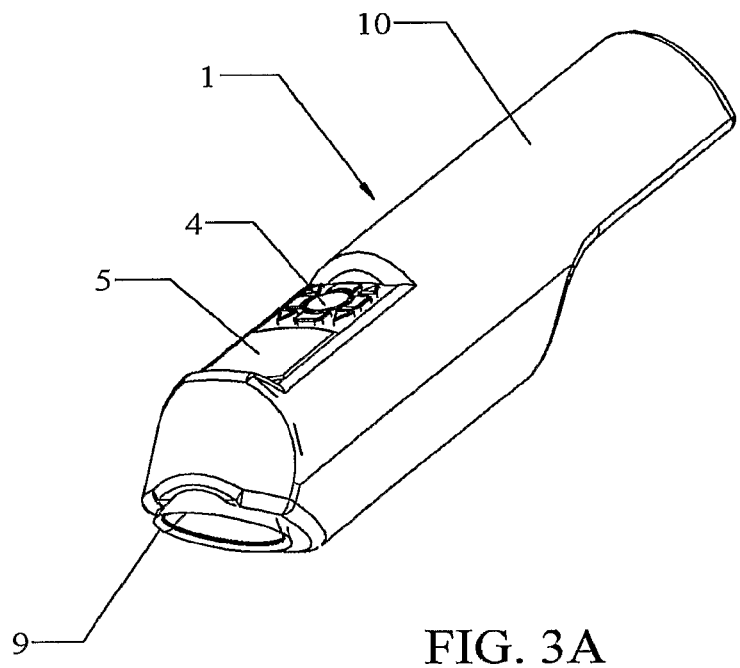
FIGS. 3A and 3B present isometric and side views illustrating an embodiment of the present invention wherein the capillary 3 is at an oblique angle relative to the nozzle 7.
Figure 3B:
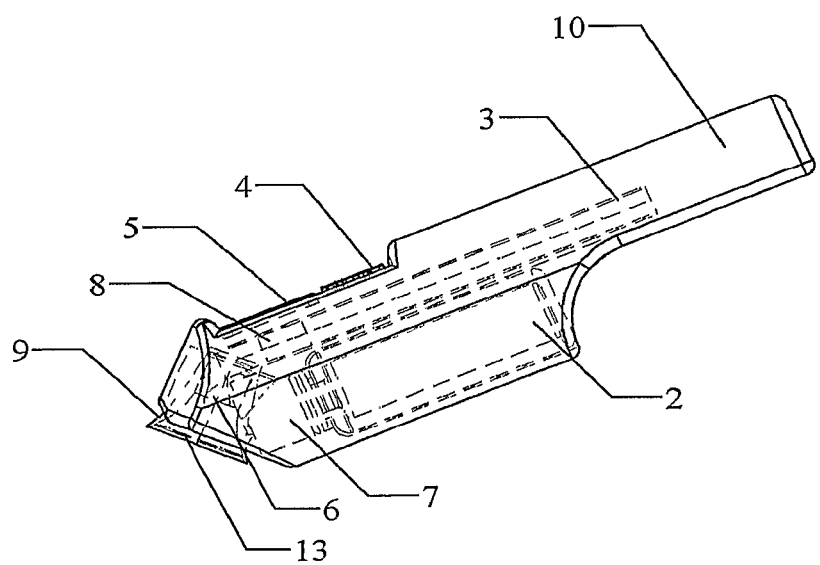

An embodiment according to the present invention (electrostatic hypospray 1) is described hereunder with reference to FIGS. 3A, and 3B. Contained within a housing 10, is a capillary 3 having a piston 8 disposed within, a nozzle 6, housing 10 having a space adapted to receive a reservoir 2 of agent, a valve 7 providing fluid communication between the reservoir 2, nozzle 6, and capillary 3, and a shield 9 surrounding the nozzle 6. Disposed within shield 9 is grounding electrode 13. Further embodiments of the present invention 1 include visual display 5 and controls 4, located on housing 10, which provide the user access to the various parameters. In further embodiments, the parameters are microprocessor controlled. The parameters would be set depending on the agent (diagnostic, or therapeutic drug, vaccine, anesthetic, or medicinal fluid) being injected. Users would insert the sealed vial, select the drug from a menu, and input the desired dose. The device would adjust all parameters to deliver the dose to the proper tissue level.

Figure 4A:
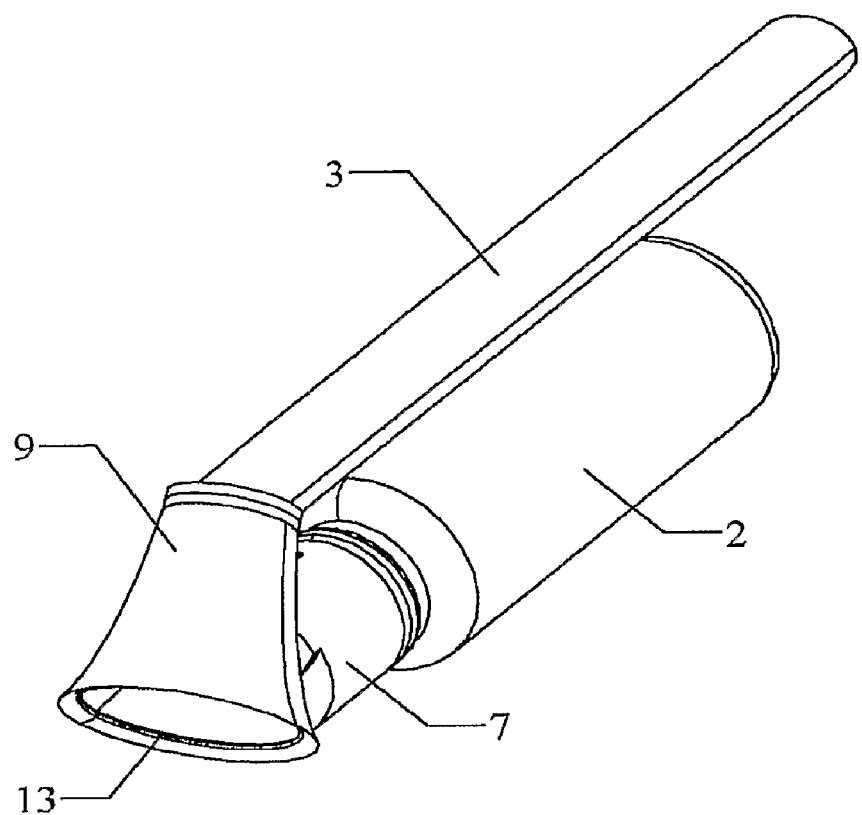
FIGS. 4A and 4B present isometric and side views of the oblique angle embodiment with the housing removed to illustrate certain inner components.
Figure 4B:
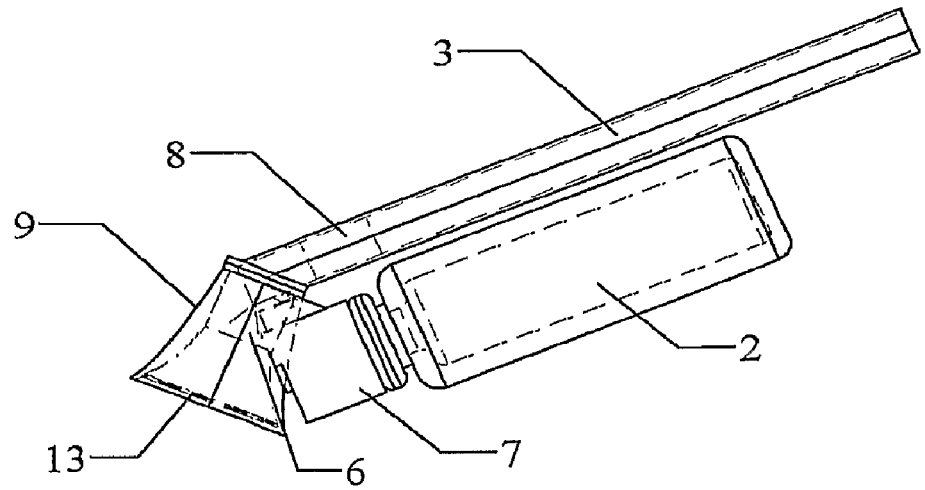
Figure 5A:
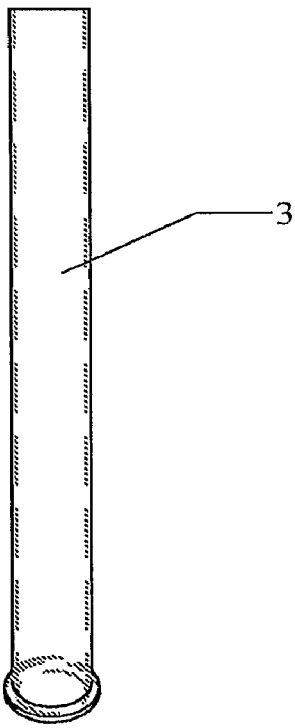
FIGS. 5A-5C present top, front, and side views of an embodiment of the capillary adapted for the oblique angle embodiment.
Figure 5B:
Figure 5C:
Figure 6:
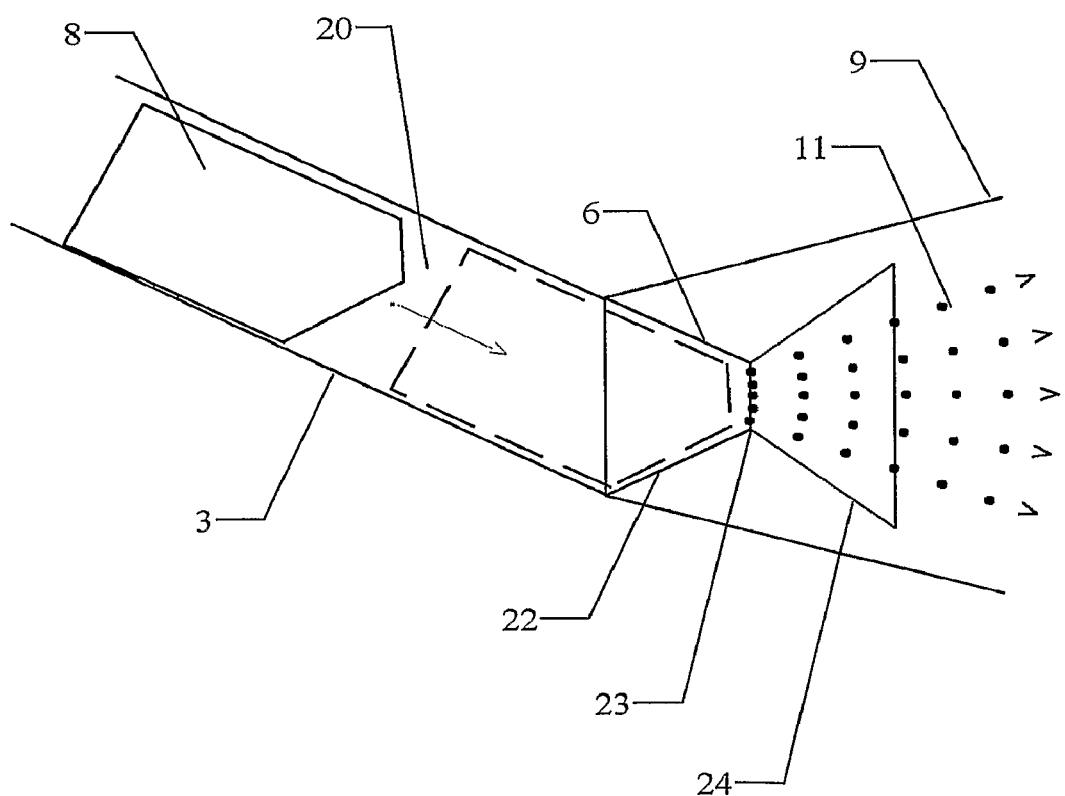
FIG. 6 illustrates the action of a piston 8 disposed in the capillary 3 to pressure atomize the fluid 20 for the oblique angle embodiment.

FIGS. 4A, and 4B, illustrate (for clarity the housing is not shown) certain embodiments of the present invention, wherein the longitudinal axis of the capillary 3 is parallel to the face of the converging section 22 of the nozzle 6 ('off-axis'). FIGS. 5A-5C illustrate an embodiment of the capillary 3 adapted to mate with the nozzle converging section 22 in such an off-axis configuration. Referring to FIG. 6, the travel of a piston 8 through the capillary 3 (during the injection phase), completely expels the fluid agent 20 from the converging section 22 through the throat 23.

Figure 7:
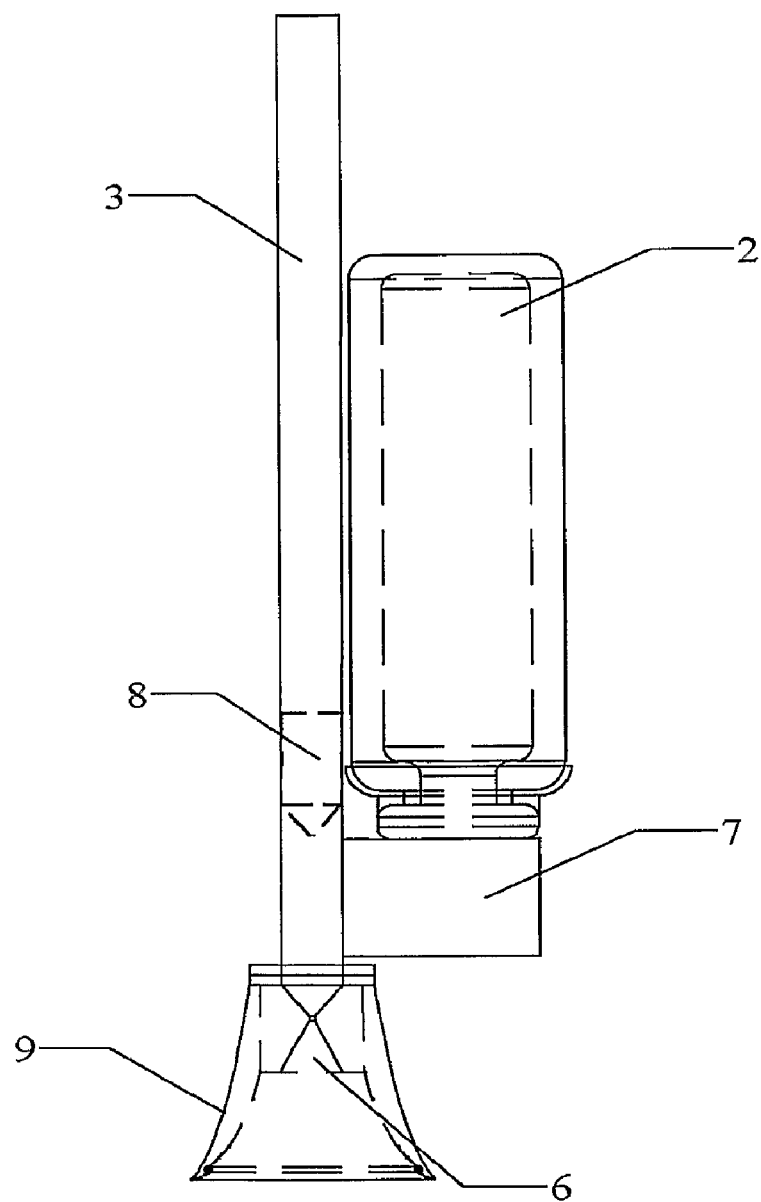
FIG. 7 is a side view (with the housing 10 removed) of an embodiment of the present invention wherein the capillary 3 is co-axial with the nozzle 7.

FIG. 7 illustrates (for clarity the housing is not shown) another embodiment of the present invention, wherein the capillary 3 longitudinal axis is coaxial with the longitudinal axis of the nozzle 6 ('co-axial').

Figure 8:
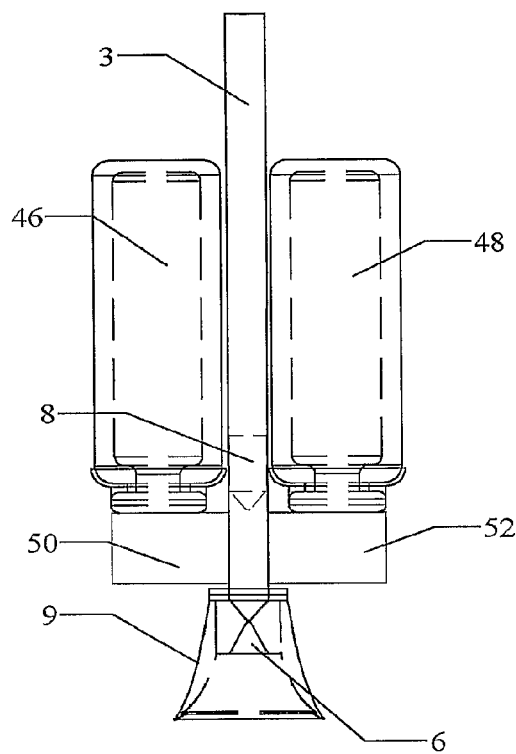
FIG. 8 illustrates an embodiment with multiple agent reservoirs

Referring to FIG. 8, an embodiment is shown with two reservoirs. Reservoir 46 is in fluid communication with capillary 3 via reservoir valve 50 which enables metering the amount of agent component delivered. Reservoir 48 is in fluid communication with capillary 3 via reservoir valve 52 which enables metering the amount of agent component delivered. The agent components from reservoirs 46 and 48 mix together in capillary 3 prior to injection.

Figure 9:
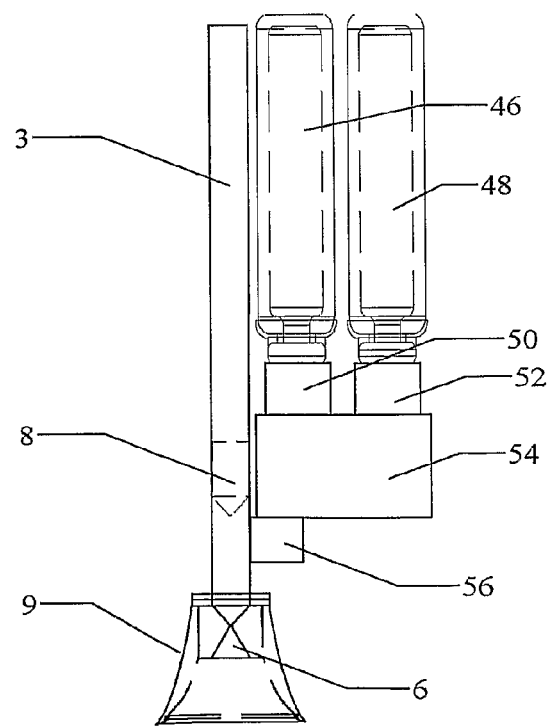
FIG. 9 illustrates another embodiment with multiple agent reservoirs

Referring to FIG. 9, another embodiment is shown with two reservoirs. Reservoir 46 is in fluid communication with mixing tank 54 via reservoir valve 50 which enables metering the amount of agent component delivered. Reservoir 48 is in fluid communication with mixing tank 54 via reservoir valve 52 which enables metering the amount of agent component delivered. Mixing tank 54 is in fluid communication with capillary 3 via valve 56.

Figure 10:
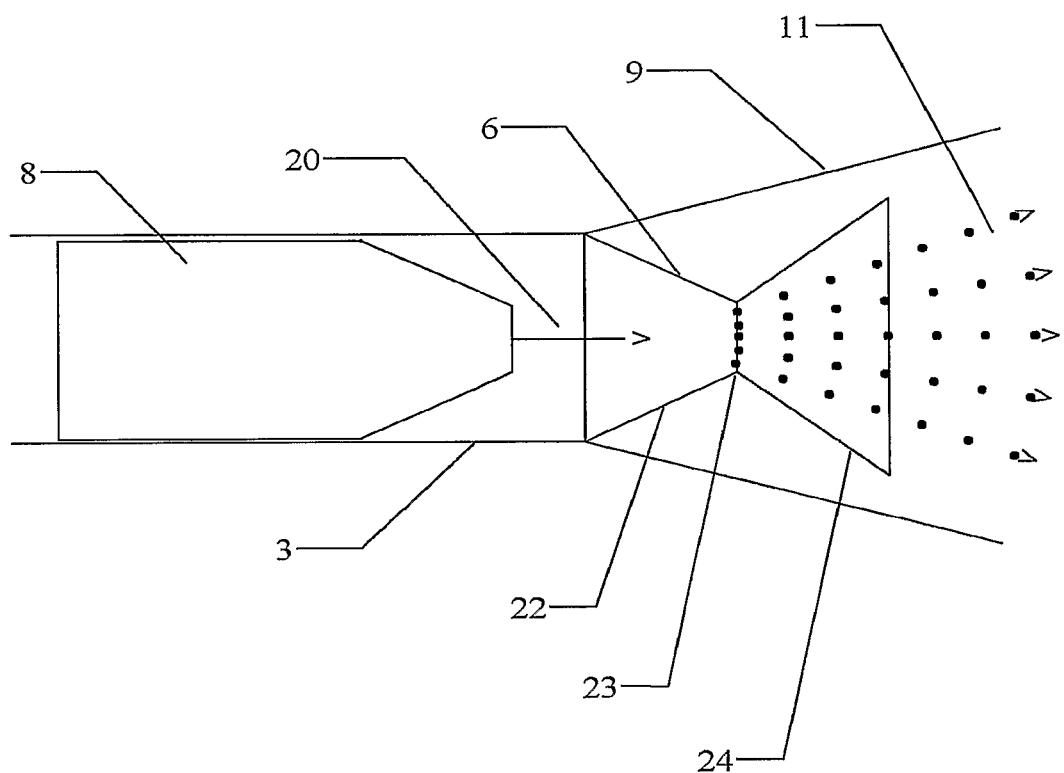
FIG. 10 illustrates the action of a piston 8 disposed in the capillary to pressure atomize the fluid 20 for the co-axial embodiment.
Figure 11A:
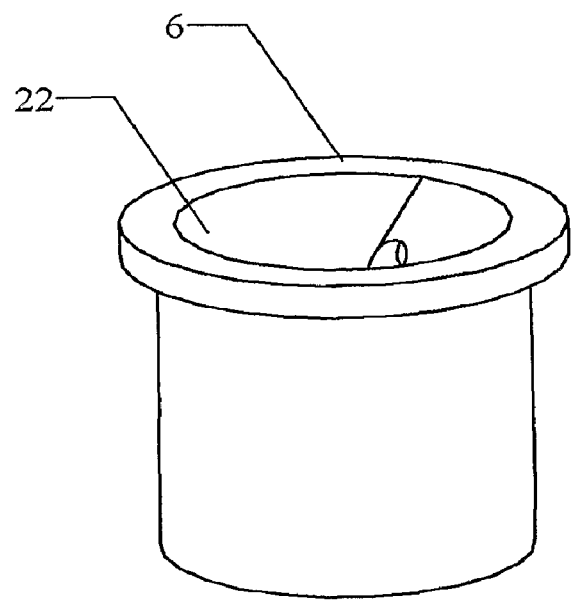
FIGS. 11A and 11B present isometric exterior views of an embodiment of the nozzle.
Figure 11B:
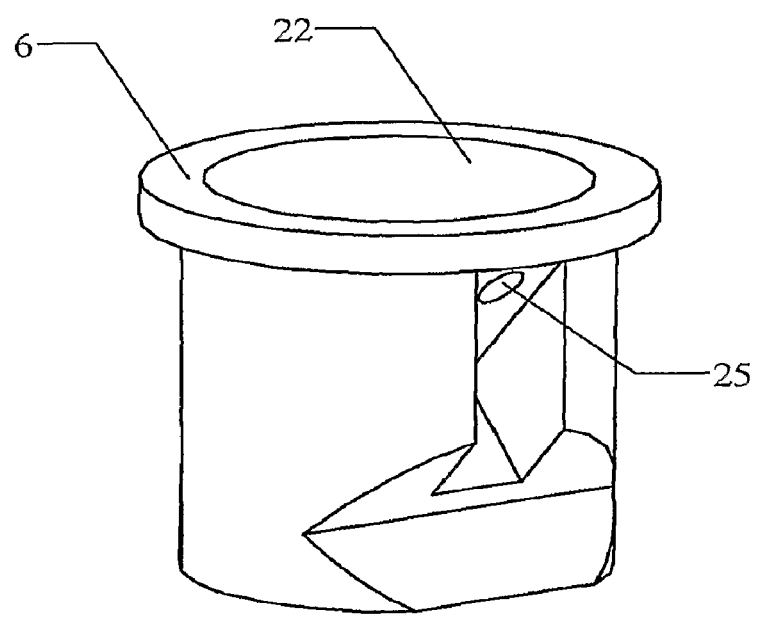

Referring to FIG. 10, the face of the piston 8 conforms to the slope of the converging section 22 of the nozzle 6, allowing complete expulsion of the fluid 20 as particle spray 11 from the converging section 22 through the throat 23 into the diverging section 24 of nozzle 6 as piston 8 moves within capillary 3. A shield 9 surrounds nozzle 6.

In embodiments of the present invention, the capillary 3 is located adjacent to (and in fluid communication with) the converging section 22 of converging nozzle 6. The capillary has a cross sectional area generally in the range of 0.2 cm$^2$ to 0.5 cm$^2$.

Referring to FIGS. 11A, 11B, 12A-12C, certain embodiments of nozzle 6 comprise converging section 22, and throat 23. In further embodiments, the nozzle has a diverging section 24 downstream of the throat region 23. The nozzle throat 23 diameter ranges generally from about 250 μm to 1.0 mm. The nozzle convergence angle ranges generally from about 15 degrees to 30 degrees. The nozzle divergence angle ranges generally from about 30 degrees to 45 degrees. Referring to FIGS. 3B, 12A-12C, certain embodiments of the nozzle 6 comprise a flow passageway 25 connecting valve 7 (not shown) with nozzle converging section 22. Nozzle 6 may further comprise a recess 26 adapted to receive a portion of valve 7. In other embodiments, portions of the diverging section 24 are straight. In various embodiments, all or portions of nozzle 6 is surrounded by shield 9 (not shown).

Fluid from the fluid reservoir may be delivered to the inventive device in various ways. In the present invention, the fluid is delivered to a pressurizing region. In certain embodiments, the fluid is delivered continuously (to allow modes of continuous spray operation). In other embodiments, the fluid is delivered in discrete amounts ('measured amounts' or 'doses), such as would be useful for injections of doses of agents. In certain embodiments, the pressurizing region comprises the converging portion of the nozzle and the capillary. In other embodiments, the pressurizing region comprises the capillary. Fluid from a vial may be withdrawn by various means, including electrostatic, electromechanical, or manual means controlling a piston disposed in the capillary. In certain embodiments, as the piston is pulled back, the resulting suction force draws a metered amount of agent through a reservoir valve into the pressurizing region. Electromechanical means to move the piston include but are not limited to: solenoids, LVDT (linear variable differential transformer), and a wire coil wrapped around the capillary to create an electromagnetic field capable of directing movement of the piston. In other embodiments, the fluid agent is delivered to the pressurizing region by a pumping means. Such pumping means may include but not be limited to: syringe pumps, piston pumps, and other pumps as would be known to one skilled in the art.

The measured amount of dose may be metered by various methods as would be known to one well skilled in the art. In certain embodiments, sensors monitor the fluid such that only the programmed quantity is withdrawn. In other embodiments, visual markings may be used to indicate proper dosage. In other embodiments, a detent stop for the piston (to prevent excess withdrawal) may be used.

The fluid agent may be pressurized by various means. In certain embodiments, a piston in the capillary is driven in the direction of the nozzle, exerting a force on the measured dose. The piston may be driven by various means well known in the art, including but not limited to electrostatic, electromechanical, manual, spring force and pneumatic. In other embodiments, the fluid dose may be pressurized by pumps, and other pressurizing means as would be known to one skilled in the art.

In certain embodiments, means for controlling flow through the nozzle throat area is present. As described earlier in certain embodiments, said means may be a valve. In other embodiments, said means comprises means to vary the cross-sectional area. In some embodiments said throat area varying means includes the ability to completely close the throat area. In other embodiments said throat area varying means does not include the ability to completely close the throat area. FIGS.

Figure 13:
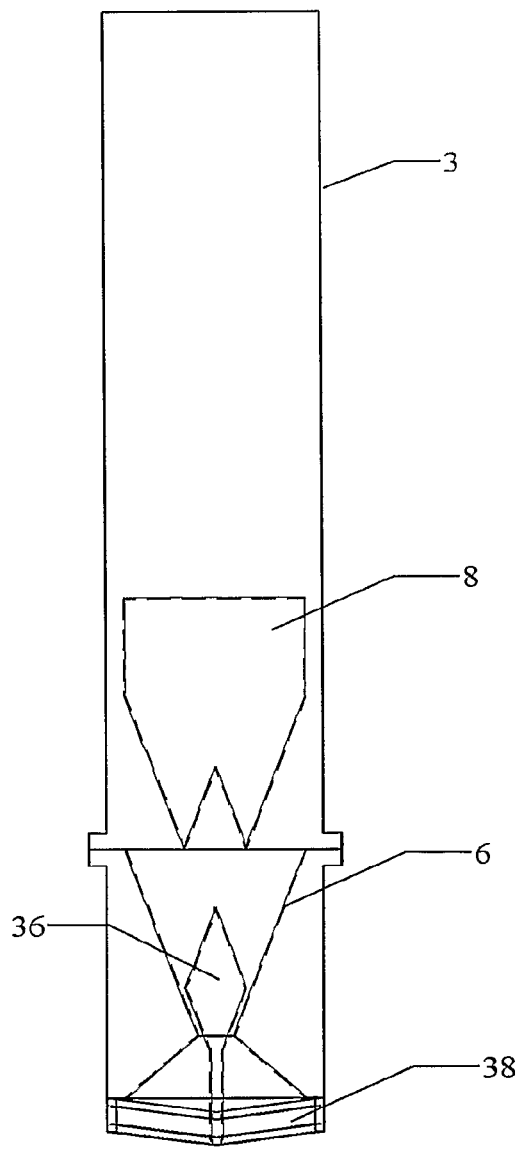
FIG. 13 illustrates an embodiment of a metering rod to vary the nozzle throat area.
Figure 14:
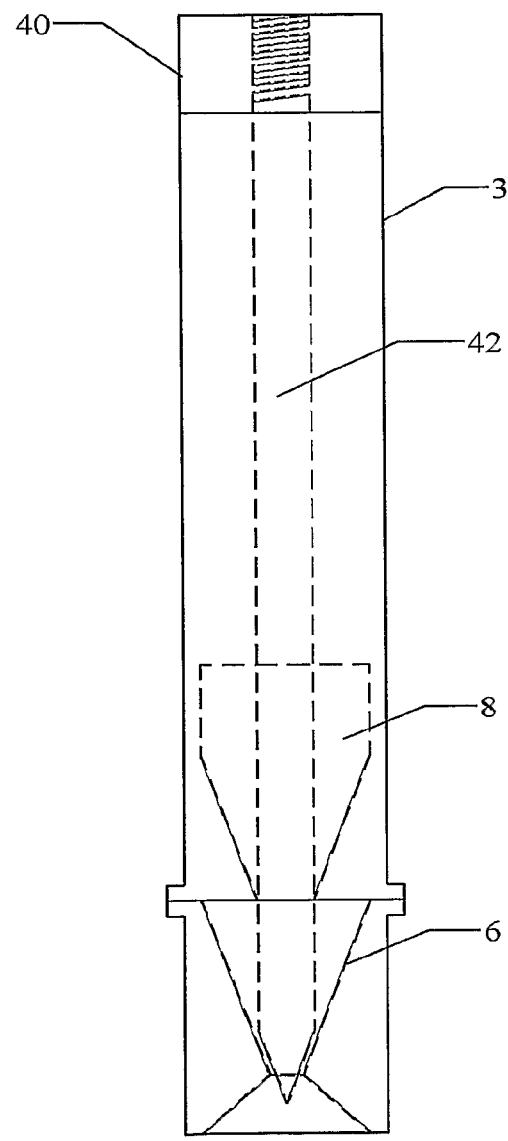
FIG. 14 illustrates another embodiment of a metering rod.

13 and 14 illustrate embodiments wherein a metering rod co-axial with the nozzle is used to vary the throat area. Decreasing the throat area generally decreases particle size, and increases particle velocity. Positioning the metering rod closer to the nozzle throat will result in an increased fluid velocity whereas positions further from the nozzle throat will reduce the fluid velocity. Referring to FIG. 13, piston 8 is disposed in capillary 3. The face of piston 8 is adapted to conform to the contour of converging section of nozzle 6, and metering rod 36. The depth to which metering rod 36 is disposed in the converging section of nozzle 6 is controlled by linkage 38. Referring to FIG. 14, piston 8 is disposed in capillary 3. The face of piston 8 is adapted to conform to the contour of converging section of nozzle 6. Metering rod 42 is disposed in capillary 3, coaxial with piston 8. The position of metering rod 42 is adjusted using adjustment screw 40. In other embodiments, the nozzle unit is interchangeable with other nozzle units having different throat diameters, and/or different convergence/divergence angles. Such nozzle units would include the nozzle and shield portion, and have fluid and power connections with the main unit (housing the capillary, pressurizing means, sensors, power source and fluid reservoir). In certain embodiments, the nozzle unit connects to the capillary via Luer interlocks, quick disconnects, or threading (e.g. nozzle would be internally threaded and capillary externally threaded).

Figure 15:
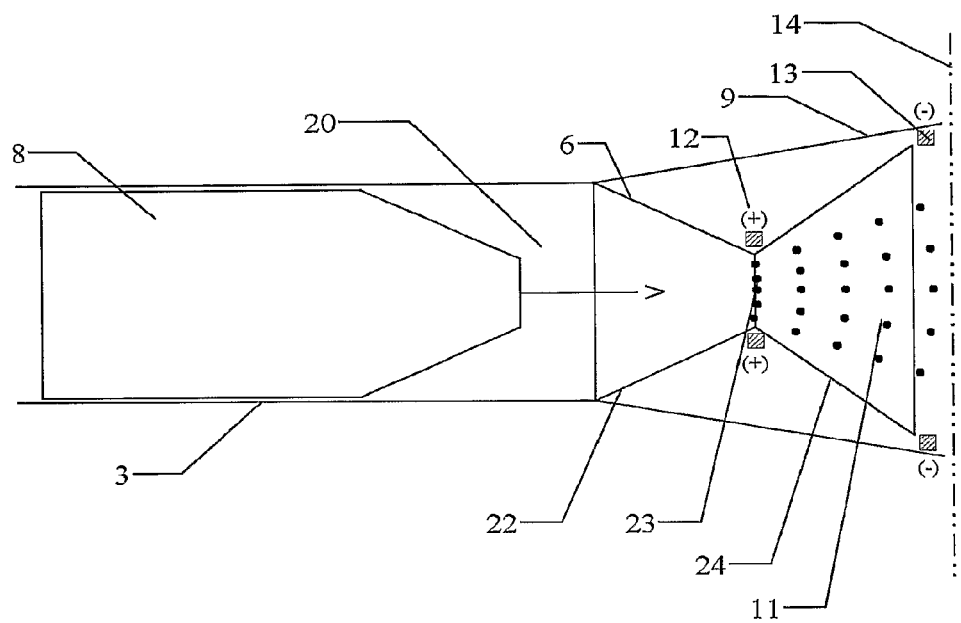
FIG. 15 illustrates an embodiment having positive and negative electrodes (12 and 13) which electrostatically spray charge the particles 11.

Referring to FIG. 15, the fluid 20 is accelerated as it flows through the converging section 22 towards the throat 23, reaching a maximum velocity at the throat 23. Upon exiting the throat 23, the fluid 20 rapidly expands due to the pressure difference across the throat 23, resulting in atomization of the fluid 20 into particles 11 imparting a finite velocity to the exiting particles 11 ('pressure atomization'). The upstream to downstream pressure ratio and throat flow area are selected according to the desired particle size and flow-rate. Particle size may be adjusted to range from the nanometer to the micron size depending on pressure ratios, and orifice size. In embodiments incorporating pressure atomization and electrostatic atomization, two phase flow can occur at the throat 23, wherein supersonic flow may result in the diverging section 24 the nozzle, depending on the pressure ratios and orifice size.

Referring to FIG. 15, a charge is induced on the spray particles by application of an electrical potential difference between a first electrode (positive electrode 12) and a second electrode (negative electrode 13) ('spray charging electrodes'), to create a non-uniform electric field between the first and second electrodes. In certain embodiments, the applied potential results in electrostatic atomization of the fluid 20 into particles 11 (enhancing the pressure atomization of the fluid), and accelerating the particles 11. In other embodiments, there is no electrostatic atomization, and the applied potential results in electrostatic spray charging only, wherein the space charge effects serve to accelerate the particles 11. In other embodiments, the applied potential serves to deform the particles, and/or increase the dispersion pattern.

Referring to FIG. 15, depth of penetration of particles 11 into target 14 (such as biological tissue) is controlled by: a) changing the distance between the nozzle 6 and the ground ring (negative electrode 13); b) adjusting the diameter of the ground ring (negative electrode 13), to change the dispersion pattern; c) changing the potential difference between the nozzle 6 and ground ring (negative electrode 13), d) adjusting the volumetric flow rate, and the fluid/particle velocity. In addition, the force in which the injection device is pressed against the target 14 will affect the depth of penetration. In further embodiments, tactile feedback from sensors (not shown) incorporated into the device allow control parameters to be adjusted to account for changes in the force in which the device is held against target 14.

In certain embodiments, the nozzle serves as the first electrode, with a grounding ring electrode as the second electrode disposed downstream of the nozzle. A exemplary ring electrode would be 2.5 cm, placed between 1 and 2 cm from the nozzle. In certain embodiments, wherein the nozzle serves as the first electrode, the entire nozzle is composed of a conductive material suitable for an electrode. In other embodiments, the converging section of the nozzle up through the throat region is composed of said conductive electrode material, with the diverging section composed of a non-conductive material. In certain embodiments, the second electrode is disposed on the shield which is composed of a non-conductive material. In other embodiments, an electrode disposed adjacent to the nozzle throat region serves as the first electrode. In certain embodiments, a positive voltage is applied to the first electrode with the second electrode grounded. In other embodiments, the first electrode is grounded and a positive voltage applied to the second electrode. In other embodiments, negative voltages are applied, or combination of positive and negative voltages. Voltage potentials are in the range of about 1 kV to 20 kV. Current is generally less than 1 micro amp.

The size, velocity, and dispersion of the particles all affect the injection area and depth of injection. Given a set convergence angle, throat diameter and divergence angle, the volumetric flow rate, particle velocity, administered volume, administration rate, and depth of drug penetration into the skin are all controlled as follows.

With a fixed capillary cross-sectional area the volumetric flow through the nozzle throat, volumetric ejection rate (VER), is varied by changing the rate at which the piston is depressed. In one embodiment where the fluid in the capillary is accelerated by only electrostatic means, this rate is dependent on the applied electric potential. It is to be understood that the velocity or acceleration profile of the piston or fluid does not necessarily need to be linear.

Pressure atomization of the fluid occurs as a result of the fluid acceleration then rapid expansion through the nozzle throat. This processes results in an inherent particle size and particle velocity. With no other influence the particle dispersion is geometrically related to the divergence angle of the nozzle. However particle size, which is influenced by the molecular weight of the fluid and fluid velocity, may effect the dispersion. That being said, larger particles will not disperse to the same degree as smaller particles. Higher fluid velocities will result in smaller particles and larger dispersion areas. The injection area, regardless of particle size and velocity, will reach an asymptotic maximum governed by the divergence angle and the distance from the dermis.

The volumetric injection rate (VIR) is defined as the rate at which a defined volume of drug penetrates the dermis. The dispersion pattern (injection area) and particle velocity determine the VIR. An increased dispersion with the velocity fixed results in an increased VIR and an increased velocity with the dispersion fixed results in an increased VIR.

Applying an electrostatic potential to the particle stream will have the following effects. A low potential difference between the ground ring and nozzle will help maintain the particle velocity. Increasing the potential difference will accelerate the particles and increase the particle dispersion (the particles will be drawn toward the ground ring). As the voltage is increased farther, the particles will deform becoming ellipsoid until the point in which the applied voltage exceeds the surface charge in the particle. When the surface charge is exceeded the particles disintegrate forming smaller particles.

When the electrostatic process increases the particle velocity and/or dispersion pattern, the VIR increases. The increased particle velocity increases the depth of penetration. The ellipsoid particles will penetrate more easily (and potentially deeper). Smaller particles with higher velocities will penetrate even farther.

In one embodiment the flow is continuous. In another embodiment the velocity of the electrostatic accelerated particles and the VIR will exceed the VER resulting in pulsatile flow.

The velocity and volumetric flow rate are related by the area in which the flow is occurring. This relationship only holds true for regions of known geometries. Volumetric flow is controlled by the initial volume of fluid and the velocity of the initial fluid acceleration in the region of constant cross-sectional area. Once the fluid exits the nozzle the volumetric flow will remain constant but the velocity and area of impact will change with respect to the applied voltage and total charge density. The total charge density at the tissue is determined by the size In certain embodiments, the first and second electrodes provide an electric field symmetric with respect to the flow axis of the nozzle, such as would be occur with ring electrodes. In other embodiments, asymmetric fields may be desirable. In one embodiment, the ground ring is constructed from two electrically isolated semicircles with the potential difference established between the semicircles. For example, one of the semicircles could be grounded, and the second at −1 kV, with the first electrode at +kV. Such an asymmetric potential field could be used to modify the spray shape from a conical shape. In other embodiments, a brief burst (few milliseconds) of alternating current (100 hz, 200 mA current, 30 to 60 Vrms) is passed across the two electrically isolated semicircle (which are in contact with the dermis) just prior to injection. This would result in electro-anesthesia thus reducing any pain associated with the injection.

Vaporization of the fluid will be dependent on the fluid velocity and fluid properties (e.g. viscosity, temperature, molecular weight).

Administration volume and rate are dependent on the dose initially loaded into the injection system. Once the dose volume is loaded the administration rate can be controlled via changing the initial acceleration or changing the charge density between the ground ring and the nozzle. The volumetric administration rate can also be varied by adjusting the particle impact area via adjusting the diameter of the ground ring.

Figure 16:
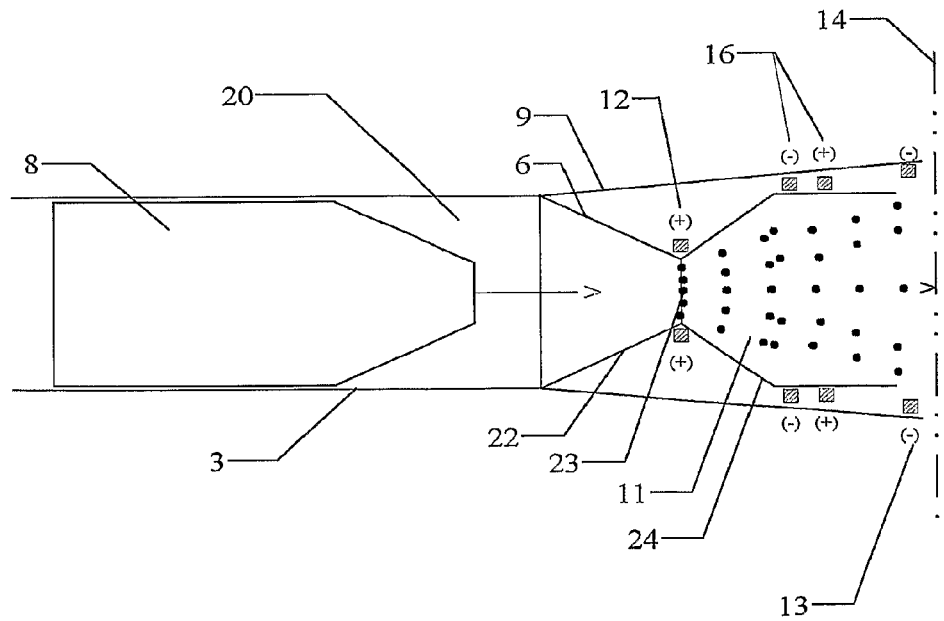
FIG. 16 illustrates an embodiment, having electrodes 16 which serve to focus and accelerate particles 11.

Referring to FIG. 16, in further embodiments, the particles pass through electric potential fields created by one or more electrodes 16 ('focusing electrodes') disposed downstream of the nozzle throat 23. The potential fields result in acceleration, focusing or combination of the foregoing actions on the particles. It is to be understood that acceleration may be positive or negative (deceleration), and that focusing is to be understood as either decreasing or increasing the dispersion of the spray. In certain embodiments, a plurality of electrodes are disposed downstream. In further embodiments, the plurality of electrodes alternate in polarity. The electrode polarity and magnitude may be unchanging with time, or time dependent. The magnitude of the potential may be such that the net velocity profile will be constant. That is, the superposition of the velocity resulting from the ejection of fluid from the capillary through the nozzle and the particle velocity resultant of the applied potential will result in near constant velocity during dermal penetration. In other embodiments, a potential difference is applied between the ground ring 13 and nozzle 6 and a second potential difference (positive or negative) is applied to the intermediate plurality of electrodes 16. In these embodiments, the plurality of intermediate electrodes 16 serves to electrostatically focus the spray 11. Increasing the potential will decrease the dispersion pattern and decreasing the potential difference will increase the dispersion pattern.

It is to be understood that a further embodiment (not shown) may utilize a combination of a mixing tank to combine constituent parts for a particular subcomponent, along with delivery of other subcomponents directly to the pressurizing chambers,

EXAMPLE 1

A 10 cc vial of insulin is inserted into an embodiment of the present invention as shown in and described with reference to FIG. 16. The capillary has a cross-sectional area of 0.3 cm². The nozzle has a throat area of 500 µm, convergence angle of 25 degrees, and divergence angle of 40 degrees. The electrostatic atomizing potential is applied between the nozzle (energized electrode) and a grounded ring electrode disposed on the shield. A plurality of focusing electrodes are disposed on the shield, adjacent to the nozzle diverging section. The operator presses a button on the control to cause 1 unit of insulin to be withdrawn from the vial. The end of the shield is pressed against the skin of the patient. The operator presses a button to energize the spray charging electrodes (selecting the mode with combined pressure atomization and electrostatic atomization), setting the voltage at 5 kV. The operator selects a delivery flow rate of 2 cc/sec. The atomization pressure is adjusted to generate droplets in the range of 50-100 nanometers. The operator presses the injection button to deliver the insulin dose to the patient.

EXAMPLE 2

Same fact pattern as Example 1, except that the operator further activates the focusing electrodes with an applied voltage of 1 to 2 kV, which slightly focuses the spray to impact a skin area of 1.5 cm² as opposed to 2.25 cm² in Example 1.

EXAMPLE 3

Same fact pattern as Example 1, except that the device uses a metering rod, as illustrated in FIG. 13, to vary the nozzle throat area. The operator reduces the throat area to an effective flow area of 250 µm via a metering rod, to increase the spray particle velocity.

Obviously numerous modifications and variations of the present invention are possible in the light of the above teachings. It is therefore to be understood that within the scope of the appended claims the invention may be practiced otherwise than as specifically described therein.

The invention claimed is:

1. A method of injecting a fluid agent into tissue, which comprises:
   delivering said fluid agent to a capillary in fluid communication with a nozzle, said nozzle having a converging section, a throat region downstream of said converging section, and a diverging section downstream of said throat region, with said capillary fluid communication comprising fluid communication with said nozzle converging section;
   pressurizing said delivered fluid agent to a level effective for pressure atomizing said pressurized fluid agent into fluid particles as said pressurized fluid agent passes through said nozzle, and for two phase flow in said delivered fluid agent to occur at said throat region;

applying a high voltage potential between a first electrode disposed adjacent to said fluid agent passing through said nozzle converging section, and a second electrode disposed downstream of said first electrode and electrically isolated from said first electrode to create a non-uniform electric field that electrostatically spray charges said fluid agent;

and directing said charged particles towards said tissue resulting in said charged particles impinging and penetrating said tissue.

2. The method according to claim 1, wherein:
said electrostatic spray charging results from said non-uniform electric field causing electrostatic atomization of said fluid agent.

3. The method according to claim 1, further comprising:
affecting the movement of said charged particles prior to impingement on said tissue, by passing said charged particles through a downstream electric potential field created by one or more focusing electrodes disposed downstream of said throat region, wherein said movement is selected from the list consisting of accelerating, decelerating, focusing, dispersing, and combination of the foregoing.

4. The method according to claim 3, wherein:
said downstream focusing electrodes alternate in polarity.

5. The method according to claim 3, wherein:
said downstream electric potential field varies with time, with said time dependent downstream field parameters selected from the list consisting of magnitude, polarity, and combination of the foregoing.

6. The method according to claim 1, wherein:
said fluid agent is derived from two or more components;
and further comprising mixing said components to form said fluid agent prior to said pressurizing step.

7. The method according to claim 6 wherein:
said mixing step is selected from the list consisting of:
a) delivering said components to a mixing tank where said mixing to form said fluid agent occurs, and
b) delivering said components to said capillary where said mixing to form said fluid agent occurs.

8. The method according to claim 1, wherein:
said fluid agent is derived from two or more components;
at least one of said components is in the dry state with each said dry state component(s) contained in a dry state component vial(s), and at least one of the other components is in the fluid state with each said fluid state component(s) contained in a fluid state component vial(s);
and further comprising:
transferring said fluid state component(s) to said dry state component vial(s),
and mixing said dry state component(s) and said fluid state component(s) to form said fluid agent.

9. The method according to claim 1, wherein:
said fluid agent is derived from two or more components;
at least one of said components is in the dry state with each said dry state component(s) contained in a dry state component vial(s), and at least one of the other components is in the fluid state with each said fluid state component(s) contained in a fluid state component vial(s);
and further comprising:
i) drawing said fluid state component(s) into said capillary,
ii) transferring said fluid state component(s) from said capillary to said dry state component vial(s), and
iii) mixing said dry state component(s) and said fluid state component(s) to form said fluid agent.

10. The method according to claim 1, wherein:
said fluid agent is an agent selected from the list consisting of therapeutic agents, diagnostic agents, and combination of the foregoing.

11. The method according to claim 1, further comprising:
varying the cross-sectional area of said throat region to vary particle size and velocity.

12. The method according to claim 1, wherein:
said fluid agent pressurizing produces nozzle upstream pressure effective to achieve supersonic flow in said particles exiting said nozzle.

13. The method according to claim 1, further comprising:
controlling particle tissue penetration by varying one or more parameters selected from the list consisting of:
a) the distance between said first and second electrodes,
b) the diameter of said second electrode, wherein said second electrode is in the shape of a ring, and
c) the potential difference between said first and second electrodes.

14. The method according to claim 1, wherein:
said second electrode is a ring electrode comprised of two electrically isolated semicircles, with said second electrode disposed to be in contact with said tissue; and
further comprising passing a brief burst of alternating current across said semicircles just prior to injection resulting in electro-anesthesia to the injection area.

15. The method according to claim 1, wherein:
said second electrode is a ring electrode comprised of two electrically isolated semicircles;
and further comprising modifying the shape of the plume of the particles exiting said nozzle by:
maintaining one semicircle at ground, and maintaining the other semicircle and said first electrode at potentials opposite in sign from each other.

16. An apparatus for injecting a fluid agent into tissue, comprising:
a nozzle having a converging section, a throat region downstream of said converging section, and a diverging section downstream of said throat region;
a capillary in fluid communication with said converging section;
a pressurizing region containing an amount of said fluid agent, wherein said pressurizing region is selected from the list consisting of: a) said nozzle's converging section, and b) said capillary;
apparatus to pressurize said fluid agent in said pressurizing region to a level effective for pressure atomizing said pressurized fluid agent into fluid particles as said pressurized fluid agent passes through said nozzle, and for two phase flow in said fluid agent to occur at said throat region, wherein said pressurizing apparatus is selected from the group consisting of
a) a piston in contact with said fluid agent and exerting force on said fluid agent, and
b) one or more pumps in fluid communication with said pressurizing region;
a first electrode disposed adjacent to said fluid agent passing through said nozzle converging section;
a second electrode disposed downstream of said first electrode and electrically isolated from said first electrode;
said first and second electrodes having a non-uniform electric field created between them, wherein said non-uniform electric field electrostatically spray charges said fluid particles; and wherein said fluid particles have velocities sufficient to impinge and penetrate said tissue, with said velocities resulting from said pressure atomization and the acceleration of the particles from the electrostatic charges on the particles.

17. The apparatus according to claim 16, wherein:
said electrostatic spray charging results from said non-uniform electric field causing electrostatic atomization of said fluid agent.

18. The apparatus according to claim 16, further comprising:
one or more focusing electrodes disposed downstream of said throat region;
said downstream focusing electrode(s) having a downstream electric potential field through which said charged particles pass, thereby affecting the movement of said charged particles prior to impingement on said tissue, wherein said movement is selected from the list consisting of accelerating, decelerating, focusing, dispersing, and combination of the foregoing.

19. The apparatus according to claim 18, wherein:
said downstream focusing electrodes alternate in polarity.

20. The apparatus according to claim 18 wherein:
said downstream electric potential field varies with time, with said time dependent downstream field parameters selected from the list consisting of magnitude, polarity, and combination of the foregoing.

21. The apparatus according to claim 16, wherein:
said fluid agent is derived from two or more components;
and further comprising:
a reservoir to hold each fluid agent component,
and a mixing tank (where mixing of said fluid agent components occur to form said fluid agent) in fluid communication with each said reservoir, and with said capillary.

22. The apparatus according to claim 16, wherein:
said fluid agent is derived from two or more components;
at least one of said components is in the dry state, and at least one of the other components is in the fluid state:
and further comprising:
i) a dry state component vial to contain each dry state component,
ii) a fluid state component vial to contain each fluid state component; and
wherein each fluid state component vial is in fluid communication with the dry state component vial to which the fluid component is desired to be added, allowing mixing of said dry state component and fluid state component to form said fluid agent.

23. The apparatus according to claim 16, wherein:
said fluid agent is derived from two or more components;
at least one of said components is in the dry state, and at least one of the other components is in the fluid state;
and further comprising:
i) a dry state component vial to contain each dry state component,
ii) a fluid state component vial to contain each fluid state component; and
wherein each fluid state component vial is in fluid communication with said capillary, and said capillary is in fluid communication with each said dry state component vial;
wherein said fluid communication between said capillary and said fluid state component vial(s) enables said fluid state component(s) to be drawn into said capillary;
wherein said fluid communication between said capillary and said dry state component vial(s) enables said fluid state component(s) to be transferred to said dry state component vial(s),
and wherein mixing of said fluid state component(s) and dry state component(s) in said dry state component vial(s) occur to form said fluid agent.

24. The apparatus according to claim 16 wherein:
said fluid agent is derived from two or more components;
and further comprising:
a reservoir to hold each fluid agent component, with each reservoir being in fluid communication with said capillary;
and wherein mixing of said fluid agent components in said capillary occurs to form said fluid agent.

25. The apparatus according to claim 16, wherein:
said fluid agent is an agent selected from the list consisting of therapeutic, diagnostic agents, and combination of the foregoing.

26. The apparatus according to claim 16, further comprising:
one or more nozzle throat area flow control elements selected from the group consisting of:
a) a valve disposed in said nozzle throat region, and
b) a metering rod disposed in and coaxial with said nozzle, said rod having an end ("throat end") proximal to said nozzle throat region, wherein varying the distance between the metering rod throat end and said nozzle throat region serves to vary the cross-sectional area of said nozzle throat.

27. The apparatus according to claim 16, wherein:
said pressurizing apparatus produces nozzle upstream pressure effective to achieve supersonic flow in said particles exiting said nozzle.

28. The apparatus according to claim 16, wherein:
particle tissue penetration is controlled by varying one or more parameters selected from the list consisting of:
a) the distance between said first and second electrodes,
b) the diameter of said second electrode, wherein said second electrode is in the shape of a ring,
c) the potential difference between said first and second electrodes, and
d) any combination of the foregoing.

29. The apparatus according to claim 16, wherein:
said second electrode is a ring electrode comprised of two electrically isolated semicircles, with said second electrode disposed to be in contact with said tissue; and
further comprising means for passing a brief burst of alternating current across said semicircles just prior to injection resulting in electro-anesthesia to the injection area.

30. The apparatus according to claim 16, wherein:
said second electrode is a ring electrode comprised of two electrically isolated semicircles;
one semicircle is at ground potential;
the other semicircle and said first electrode are at potentials opposite in sign from each other, resulting in modifying the shape of the plume of the particles exiting said nozzle.

* * * * *